US012022995B2

(12) United States Patent
Sueyasu et al.

(10) Patent No.: US 12,022,995 B2
(45) Date of Patent: Jul. 2, 2024

(54) ENDOSCOPE AND METHOD OF ATTACHING LONG MEMBER

(71) Applicant: OLYMPUS CORPORATION, Tokyo (JP)

(72) Inventors: Hidetada Sueyasu, Hino (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 825 days.

(21) Appl. No.: 17/028,092

(22) Filed: Sep. 22, 2020

(65) Prior Publication Data

US 2021/0093162 A1 Apr. 1, 2021

Related U.S. Application Data

(63) Continuation of application No. PCT/JP2018/046341, filed on Dec. 17, 2018.

(30) Foreign Application Priority Data

Mar. 28, 2018 (JP) .................................. 2018-061757

(51) Int. Cl.
*A61B 1/00* (2006.01)
*A61B 1/018* (2006.01)

(52) U.S. Cl.
CPC ...... *A61B 1/00087* (2013.01); *A61B 1/00098* (2013.01); *A61B 1/00121* (2013.01); *A61B 1/018* (2013.01)

(58) Field of Classification Search
CPC . A61B 1/00087; A61B 1/018; A61B 1/00066; A61B 1/00098; A61B 1/00121; A61B 1/001288; A61B 1/0057

(Continued)

(56) References Cited

U.S. PATENT DOCUMENTS

| 5,460,168 A | * | 10/1995 | Masubuchi | ........ A61B 1/00098 |
| | | | | 600/107 |
| 6,699,183 B1 | * | 3/2004 | Wimmer | .............. A61B 1/0057 |
| | | | | 600/149 |

(Continued)

FOREIGN PATENT DOCUMENTS

| JP | 06-315456 A | 11/1994 |
| JP | 07-111967 A | 5/1995 |

(Continued)

OTHER PUBLICATIONS

International Search Report dated Mar. 26, 2019 received in PCT/JP2018/046341.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

An endoscope includes a connector for connecting a movable body and a long member. The connector includes: an open-close member having a distal end portion and a proximal end portion which are opened or closed by swinging about a predetermined fulcrum, the proximal end portion having a holding portion which holds the long member when the proximal end portion is closed, the distal end portion having an engaging portion which projects outwardly in a radial direction of the distal end portion and is engageable with an inner side of the movable body; and a locking member which moves in a longitudinal direction outwardly in a radial direction of the open-close member, and locks the proximal end portion of the open-close member and the movable body with each other in a state where the long member is held.

20 Claims, 13 Drawing Sheets

(58) Field of Classification Search
USPC .......................................................... 600/107
See application file for complete search history.

(56) References Cited

U.S. PATENT DOCUMENTS

| | | | | |
|---|---|---|---|---|
| 7,846,090 B2* | 12/2010 | Pilvisto | .............. | A61B 1/00098 600/149 |
| 8,604,742 B2* | 12/2013 | Farritor | .................. | A61B 34/30 604/95.01 |
| 2016/0089125 A1* | 3/2016 | Morimoto | .......... | A61B 1/00098 600/107 |
| 2017/0215704 A1 | 8/2017 | Tsumaru | | |
| 2020/0054195 A1* | 2/2020 | Akhoondi | .......... | A61B 1/00066 |
| 2023/0126521 A1* | 4/2023 | Isobe | ................ | A61B 1/00128 600/107 |
| 2023/0157523 A1* | 5/2023 | Teatini | ............... | A61B 1/00098 600/107 |

FOREIGN PATENT DOCUMENTS

| | | | |
|---|---|---|---|
| JP | 2000-237120 A | | 9/2000 |
| JP | 2018-198731 A | | 12/2018 |
| WO | 2016/067974 A1 | | 5/2016 |
| WO | WO-2021193693 A1 | * | 9/2021 |

* cited by examiner

ENDOSCOPE AND METHOD OF ATTACHING LONG MEMBER

CROSS REFERENCE TO RELATED APPLICATION

This application is a continuation application of PCT/JP2018/046341 filed on Dec. 17, 2018 and claims benefit of Japanese Application No. 2018-061757 filed in Japan on Mar. 28, 2018, the entire contents of which are incorporated herein by this reference.

BACKGROUND OF THE INVENTION

1. Field of the Invention

The present invention relates to an endoscope and a method of attaching a long member.

2. Description of the Related Art

Conventionally, there has been known an endoscope where a treatment instrument which is inserted into an insertion section distal end portion from a treatment instrument insertion opening is raised by an operation member such as a treatment instrument raising base (forceps elevator) mounted on the insertion section distal end portion, and the treatment instrument is guided to a treatment portion in a subject. The treatment instrument raising base is connected to an operation knob by a wire which passes through an insertion section, and raised or lowered in accordance with the advancing and retracting movement of the wire corresponding to an operation of the operation knob. After used in the subject, the treatment instrument raising base and the wire are detached from the endoscope and are cleaned. After the cleaning, the treatment instrument raising base and the wire are again attached to the endoscope.

For example, Japanese Patent Application Laid-Open Publication No H6-315456 discloses an endoscope where a treatment instrument raising base can be raised by way of a wire. In attaching the wire to an operation section of the endoscope, a user makes the wire pass through a guide conduit and be protruded from an operation section side, the protruded wire is fixed to a connecting member by fastening a fixing screw, the connecting member engages with a transmission rod connected to the operation section, and a cap is mounted on an outer peripheral portion of the connecting member.

SUMMARY OF THE INVENTION

According to an aspect of the present invention, there is provided an endoscope which includes: an operation member disposed on an insertion section inserted into a lumen, the operation member being configured to operate by an operation from an outside, a long member connected to the operation member, the long member being configured to move in a longitudinal direction of the insertion section so as to operate the operation member, a movable body mounted on an operation section connected to the insertion section, the movable body being configured to move in the longitudinal direction, an operation knob mounted on the operation section, the operation knob being configured to move the movable body by the operation from the outside, and a connector for connecting the movable body and the long member to each other, wherein the connector includes: an open-close member having a distal end portion and a proximal end portion which are opened and closed by swinging about a predetermined fulcrum, the proximal end portion having a holding portion which holds the long member when the proximal end portion is closed, the distal end portion having an engaging portion which projects outwardly in a radial direction of the distal end portion and is engageable with an inner side of the movable body; and a locking member configured to move in the longitudinal direction outwardly in a radial direction of the open-close member, and to lock the proximal end portion of the open-close member and the movable body with each other in a state where the long member is held.

According to another aspect of the present invention, there is provided a method of attaching a long member, the method including: opening a proximal end portion of an open-close member and closing a distal end portion of the open-close member by swinging the open-close member about a predetermined fulcrum; inserting the long member into the open-close member, the proximal end portion of the open-close member being opened; inserting the distal end portion into a movable body connected to an operation section, the distal end portion being closed; closing the proximal end portion which is opened and opening the distal end portion which is closed by moving a locking member in a longitudinal direction outside in a radial direction of the open-close member to make the open-close member engage with the locking member, locking the movable body by the distal end portion which is opened, and holding the long member by the proximal end portion which is closed.

DETAILED DESCRIPTION OF THE PREFERRED EMBODIMENTS

An embodiment of the present invention is described with reference to drawings hereinafter.

(Configuration of Endoscope 1)

Figure 1:
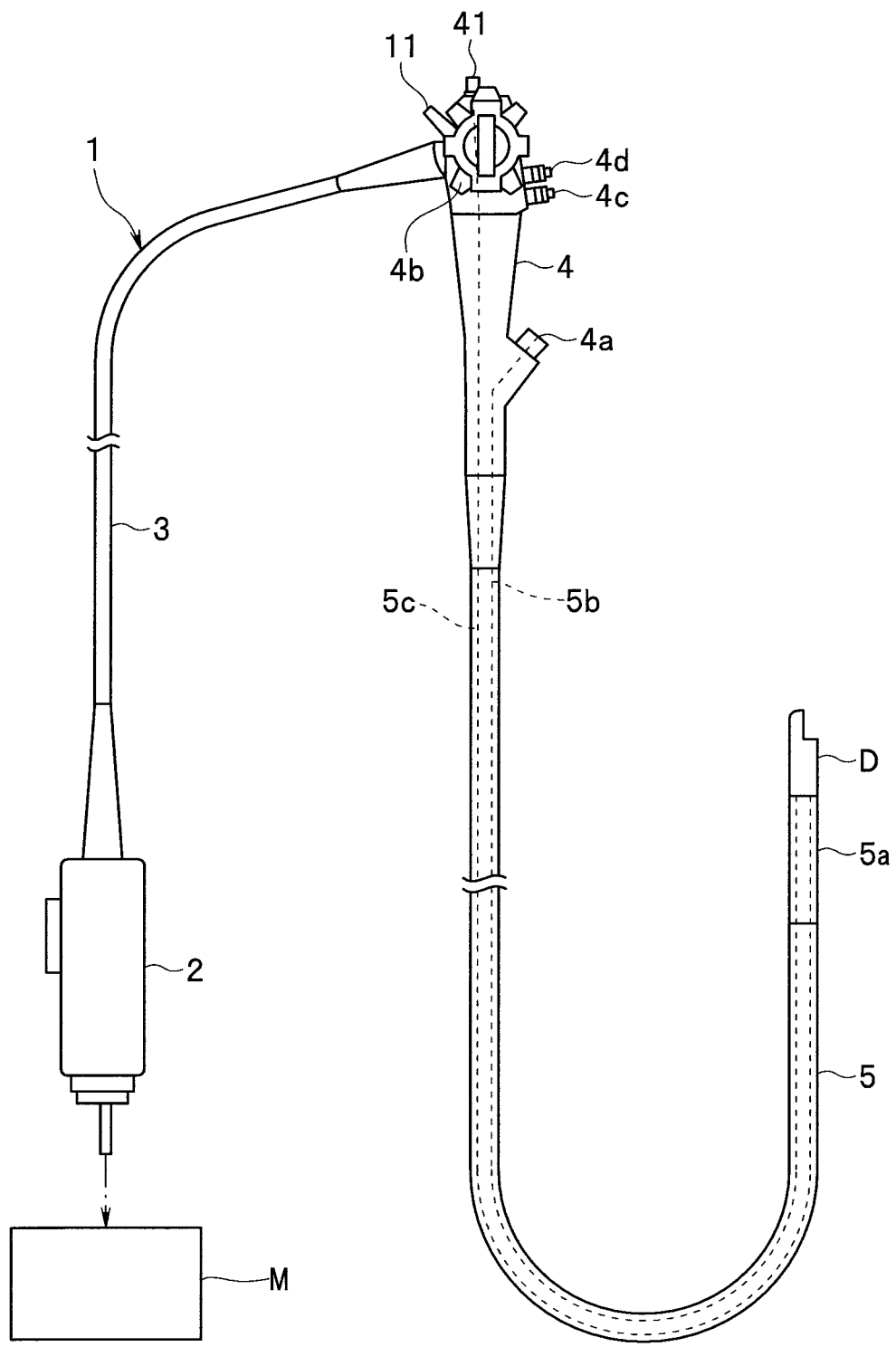
FIG. 1 is an explanatory diagram describing one example of a schematic configuration of an endoscope according to an embodiment of the present invention.

FIG. 1 is an explanatory diagram describing one example of a schematic configuration of an endoscope 1 according to an embodiment of the present invention.

The endoscope 1 includes a scope connector 2, a universal cord 3 extending from the scope connector 2, an operation section 4 mounted on the universal cord 3, an insertion section 5 continuously connected to a distal end side of the operation section 4, and an insertion section distal end portion D.

The scope connector 2 is configured to be connected to an endoscope apparatus body M such as a power source or a control device, for example.

Various conduits, signal lines and optical fibers are disposed in the universal cord 3, and the universal cord 3 connects the scope connector 2 and the operation section 4 to each other.

The operation section 4 is configured to perform various operations of the endoscope 1. The operation section 4 includes a treatment instrument insertion opening 4a, an angle knob 4b, an air/water feeding button 4c, and a suction button 4d.

A treatment instrument T (FIG. 2) can be inserted into the treatment instrument insertion opening 4a. The treatment instrument T can be protruded from an insertion section distal end portion D after passing through the insertion section 5. The treatment instrument T is a forceps, for example.

The angle knob 4b is connected to a bending portion 5a of the insertion section 5 by a wire for bending, and the angle knob 4b can input an instruction of bending the bending portion 5a in accordance with an operation by a user.

The air/water feeding button 4c can input an air feeding instruction or a liquid feeding instruction to a nozzle 6c of the insertion section distal end portion D from the endoscope apparatus body M in accordance with an operation by the user.

The suction button 4d can input a suction instruction of a suction object to the endoscope apparatus body M from an opening portion 7 of the insertion section distal end portion D in accordance with an operation by the user.

The insertion section 5 is formed in an elongated shape, and is configured to be inserted into the inside of a lumen of a subject. The insertion section 5 has the bending portion 5a, a treatment instrument conduit 5b and a guide conduit 5c.

The bending portion 5a is disposed in the vicinity of the insertion section distal end portion D, and is bent by operating the angle knob 4b To allow the treatment instrument T to pass, the treatment instrument conduit 5b is disposed in the insertion section 5, and the treatment instrument insertion opening 4a and the insertion section distal end portion D are made to communicate with each other by the treatment instrument conduit 5b.

The guide conduit 5c is disposed in the operation section 4 and the insertion section 5 for allowing the wire W which is a long member to pass, and the operation section 4 and the insertion section distal end portion D are communicated with each other by the guide conduit 5c.

In the insertion section 5, various conduits, signal lines and optical fibers are disposed besides the treatment instrument conduit 5b and the guide conduit 5c. However, the description of the conduits, the signal lines and the optical fibers is omitted in the embodiment.

Figure 2:
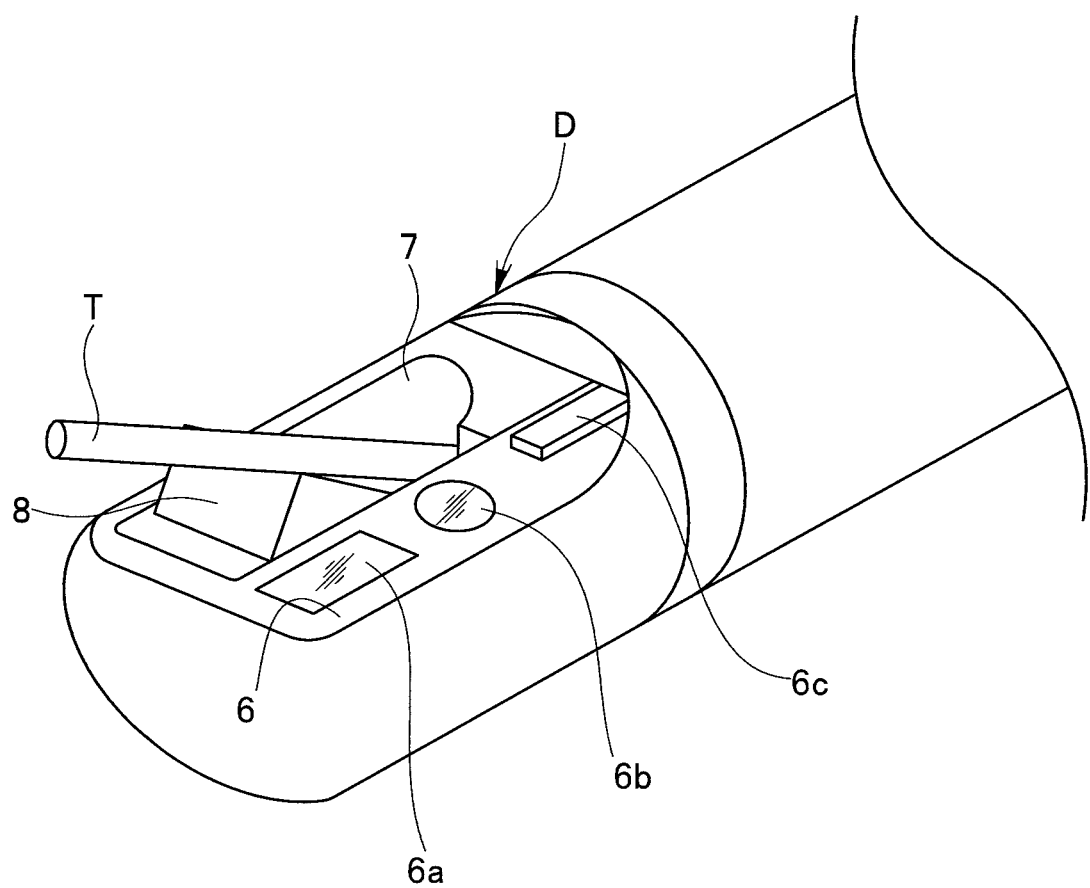
FIG. 2 is an explanatory diagram describing one example of a configuration of a distal end portion of an insertion section of the endoscope according to the embodiment of the present invention.

FIG. 2 is an explanatory diagram describing the configuration of the insertion section distal end portion D of the endoscope 1 according to the embodiment of the present invention.

As shown in FIG. 2, the insertion section distal end portion D is a rigid member and is formed in a cylindrical shape. The insertion section distal end portion D has a flat portion 6, the opening portion 7, and a treatment instrument raising base 8 which is an operation member.

The flat portion 6 is formed by flattening a portion of an outer peripheral portion of the insertion section distal end portion D. An illumination window 6a, an observation window 6b and a nozzle 6c are disposed on the flat portion 6.

The illumination window 6a has an optical lens, and irradiates a subject with an illumination light guided from a light source of the endoscope apparatus body M.

The observation window 6b receives a return light from the subject, and projects the return light to an image pickup device not shown. The image pickup device converts the return light into an image pickup signal, and outputs the image pickup signal to the endoscope apparatus body M The nozzle 6c ejects a gas or a liquid fed by the endoscope apparatus body M.

The opening portion 7 is formed on an outer peripheral portion of the insertion section distal end portion D. The opening portion 7 communicates with the treatment instrument conduit 5b and the guide conduit 5c.

The treatment instrument raising base 8 is disposed in the opening portion 7 rotatably about a proximal end portion of the treatment instrument raising base 8. A distal end portion of the treatment instrument raising base 8 is connected to a wire W which passes through the guide conduit 5c. The treatment instrument raising base 8 is raised or lowered in accordance with an advancing or retracting movement of the wire W, and guides the treatment instrument T which passes through the treatment instrument conduit 5b such that the treatment instrument T protrudes in an outer peripheral direction of the insertion section distal end portion D.

That is, the treatment instrument raising base 8 is disposed in the insertion section 5 inserted into a lumen, and is operated in accordance with an operation from the outside. The treatment instrument raising base 8 is operated so as to change a direction of the treatment instrument T which passes through the insertion section 5.

(Configuration of Operation Mechanism P)

Figure 3:
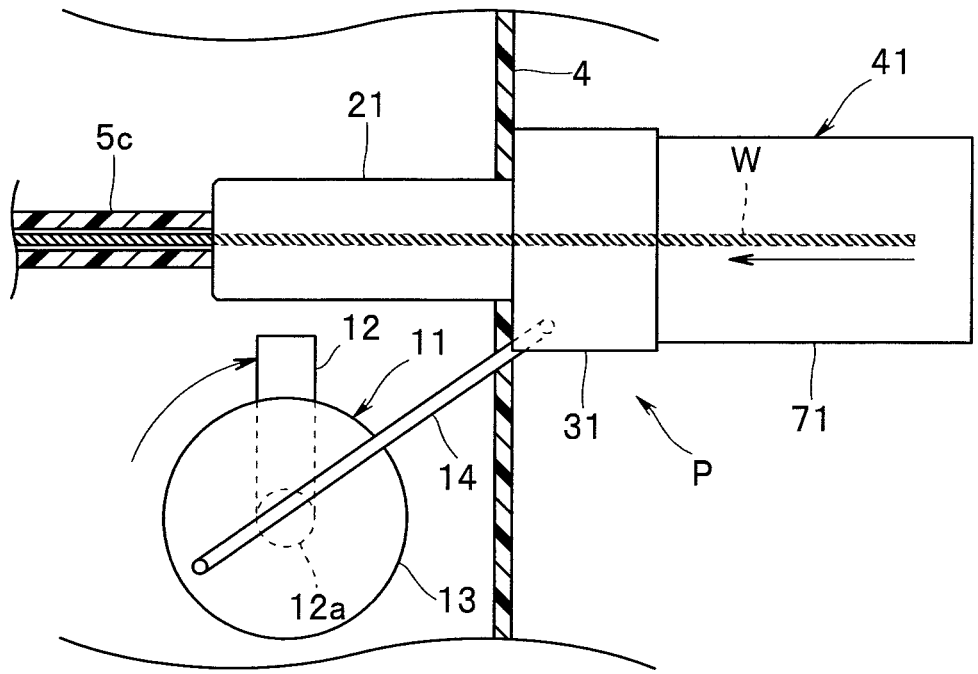
FIG. 3 is an explanatory diagram describing one example of an operation mechanism of the endoscope according to the embodiment of the present invention.
Figure 4:
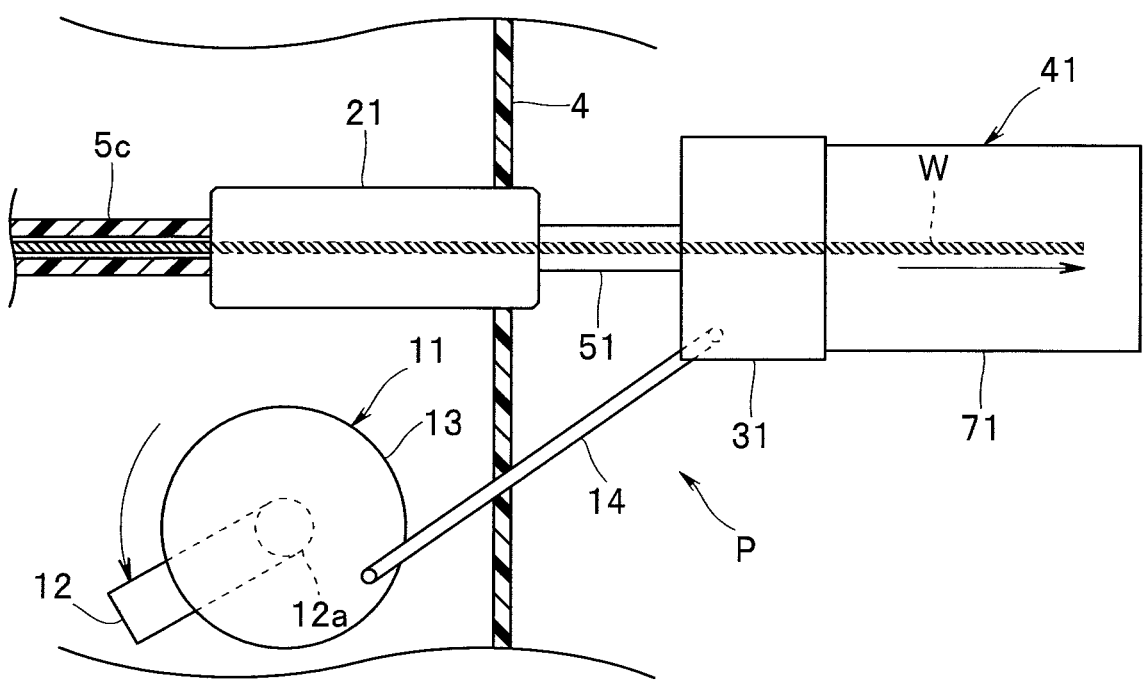
FIG. 4 is an explanatory diagram describing one example of the operation mechanism of the endoscope according to the embodiment of the present invention.

FIG. 3 and FIG. 4 are explanatory diagrams describing one example of an operation mechanism P of the endoscope 1 according to the embodiment of the present invention.

The operation mechanism P is configured to raise or lower the treatment instrument raising base 8 in accordance with an operation of the operation section 4. The operation mechanism P includes an operation knob 11, a cylinder 21 and a ring 31 which is a movable body.

The operation knob 11 is disposed in the operation section 4. The operation knob 11 can input an instruction of instructing raising or lowering of the treatment instrument raising base 8 in accordance with a rotation operation by a user. The operation knob 11 has a knob body 12, a rotary body 13 and a rod 14.

The knob body 12 is mounted on the operation section 4 such that the knob body 12 is rotatable about a rotary shaft 12a. A stopper which stops the rotated knob body 12 by abutting may be mounted on the operation section 4.

The rotary shaft 12a is connected to the rotary body 13 at the center position of the rotary body 13, for example, and a rotational force is transmitted from the rotary shaft 12a.

One end of the rod 14 is rotatably connected to a periphery portion of the rotary body 13, and the other end of the rod 14 is rotatably connected to the ring 31. The rod 14 converts a rotary movement of the rotary body 13 into a linear movement, and transmits the linear movement to the ring 31.

Although the wire W is not particularly limited, the wire is formed of a metal stranded wire, for example. A terminal portion Wt of the wire W on a proximal end side is formed of a rigid material such as metal. The wire W has a stepped portion Ws of a small diameter so as to be gripped in a vicinity of the terminal portion Wt (see FIG. 8). The stepped portion Ws constitutes an open-close member engaging portion. The wire W is connected to the operation member, and operates the operation member by moving in a longitudinal direction of the insertion section 5. The open-close member engaging portion is configured to engage with a holding portion 64 described later.

Figure 7:
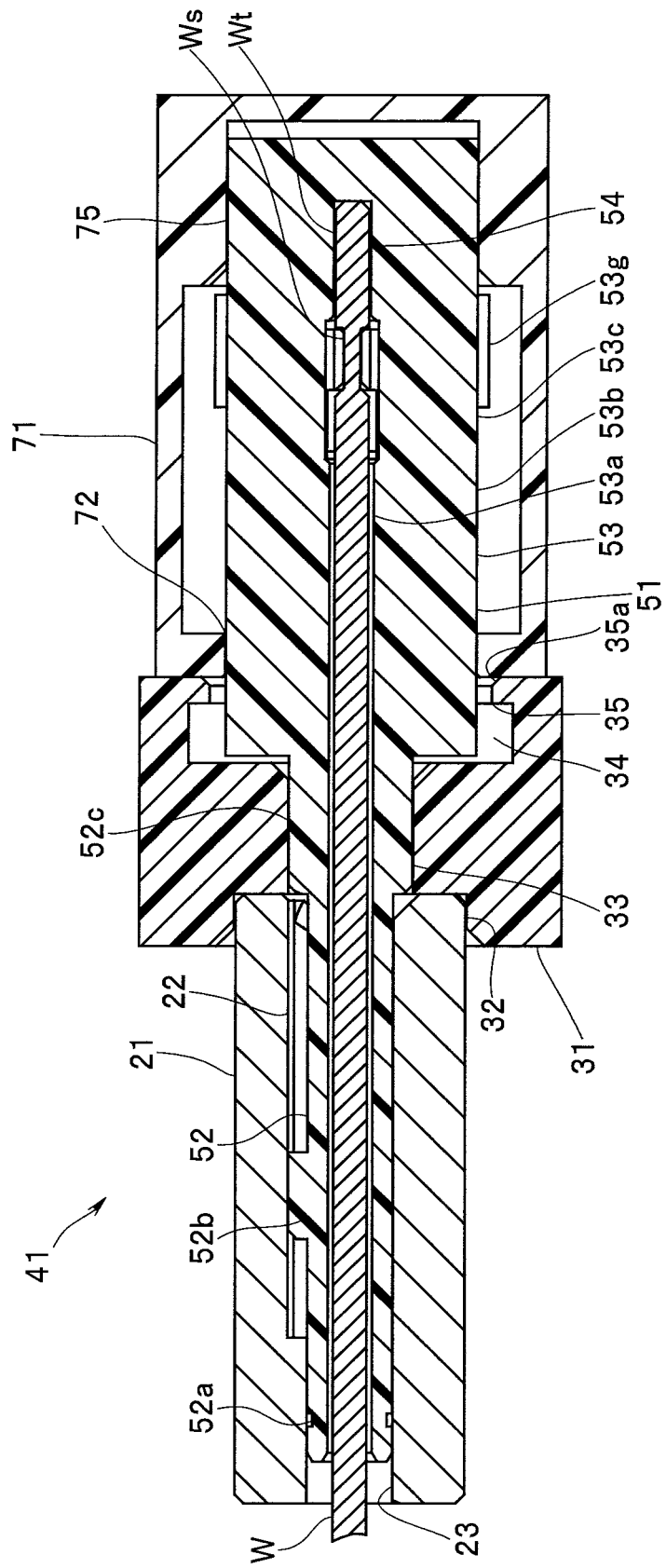
FIG. 7 is a cross-sectional view taken along a line VII-VII in FIG. 5 according to the embodiment of the present invention.

Although the cylinder 21 is not particularly limited, the cylinder 21 is made of metal, for example, and is formed in a cylindrical shape. A distal end portion of the cylinder 21 is mounted on the guide conduit 5c, and the cylinder 21 communicates with the guide conduit 5c. As shown in FIG. 7, the cylinder 21 has a rotation stopper groove 22. The rotation stopper groove 22 extends from a proximal end portion of the cylinder 21 along an insertion direction of the support member 51 on an inner peripheral surface of the cylinder 21.

Although the ring 31 is not particularly limited, the ring 31 is made of resin, for example. The rod 14 is rotatably connected to an outer peripheral portion of the ring 31, and the ring 31 performs an advancing and retracting movement in a distal end direction or in a proximal end direction by the rod 14. The ring 31 has a cylinder mounting portion 32, a support member mounting portion 33, a hook accommodating portion 34, and an inwardly directed flange 35.

The cylinder mounting portion 32 is disposed at a center portion of the ring 31 on a distal end side, and has a recessed shape which conforms with an outer peripheral surface of the cylinder 21. The cylinder mounting portion 32 is detachably mounted on an outer side of a proximal end portion of the cylinder 21.

A support member mounting portion 33 extends from a proximal end side of the cylinder mounting portion 32 in a longitudinal direction. The support member mounting portion 33 has an inner peripheral surface whose diameter is smaller than a diameter of the cylinder mounting portion 32.

The hook accommodating portion 34 extends from a proximal end side of the support member mounting portion 33 in a longitudinal direction. The hook accommodating portion 34 has an inner peripheral surface whose diameter is larger than the diameter of the support member mounting portion 33

The inwardly directed flange 35 is disposed on a proximal end side of the hook accommodating portion 34. The inwardly directed flange 35 is formed by protruding an inner peripheral surface on a proximal end side of the book accommodating portion 34 inwardly in a radial direction. The inner peripheral surface of the inwardly directed flange 35 has a diameter smaller than the diameter of the hook accommodating portion 34. Tapered guides 35a which guide the entrance of the open-close members 61 are formed on the inner peripheral surface of the inwardly directed flange 35 on a proximal end side.

In other words, the ring 31 is disposed in the operation section 4 connected to the insertion section 5, and moves in the longitudinal direction. The operation knob 11 is mounted on the operation section 4, and moves the ring 31 by an operation performed from the outside.

As shown in FIG. 3 and FIG. 4, when a user rotates the knob body 12 about the rotary shaft 12a, the rod 14 converts the rotary movement into the linear movement, and advances or retracts the ring 31 and the connector 41 mounted on the ring 31. When the connector 41 moves in a distal end direction, the wire W connected to the connector 41 is also moved in the distal end direction so as to lower the treatment instrument raising base 8 (see FIG. 3). When the connector 41 moves in a proximal end direction, the wire W is also moved in the proximal end direction so as to raise the treatment instrument raising base 8 (see FIG. 4)

(Configuration of Connector 41)

Next, the configuration of the connector 41 is described.

Figure 5:
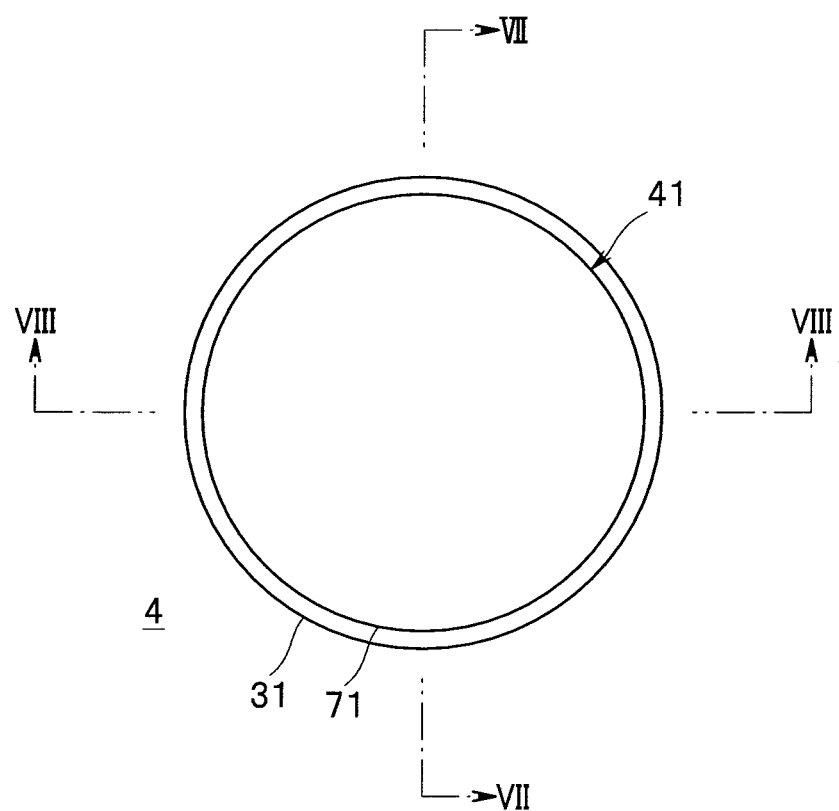
FIG. 5 is a view showing a proximal end surface of a connector of the endoscope according to the embodiment of the present invention.
Figure 6:
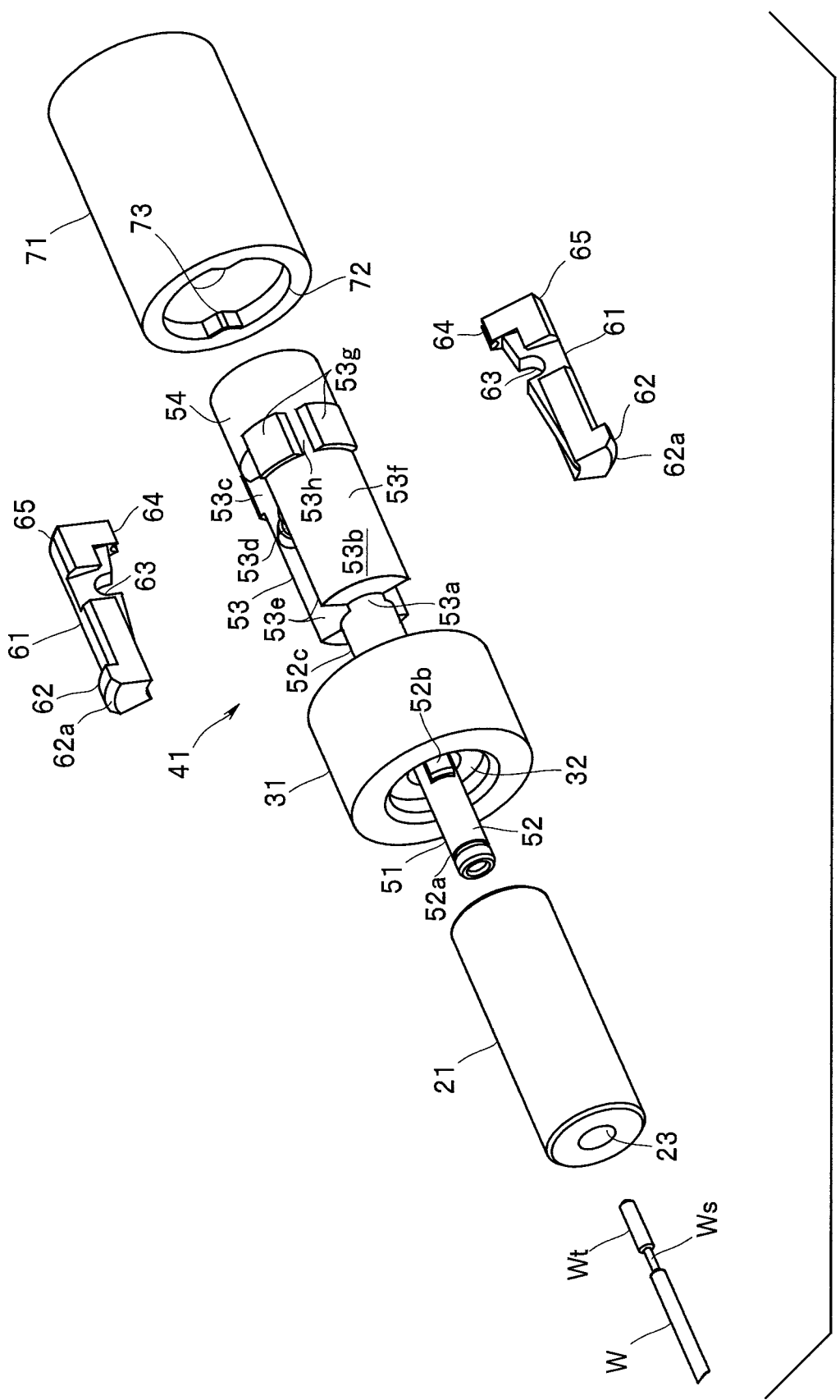
FIG. 6 is an exploded perspective view showing one example of a wire, a cylinder, a ring and the connector of the endoscope according to the embodiment of the present invention.
Figure 8:
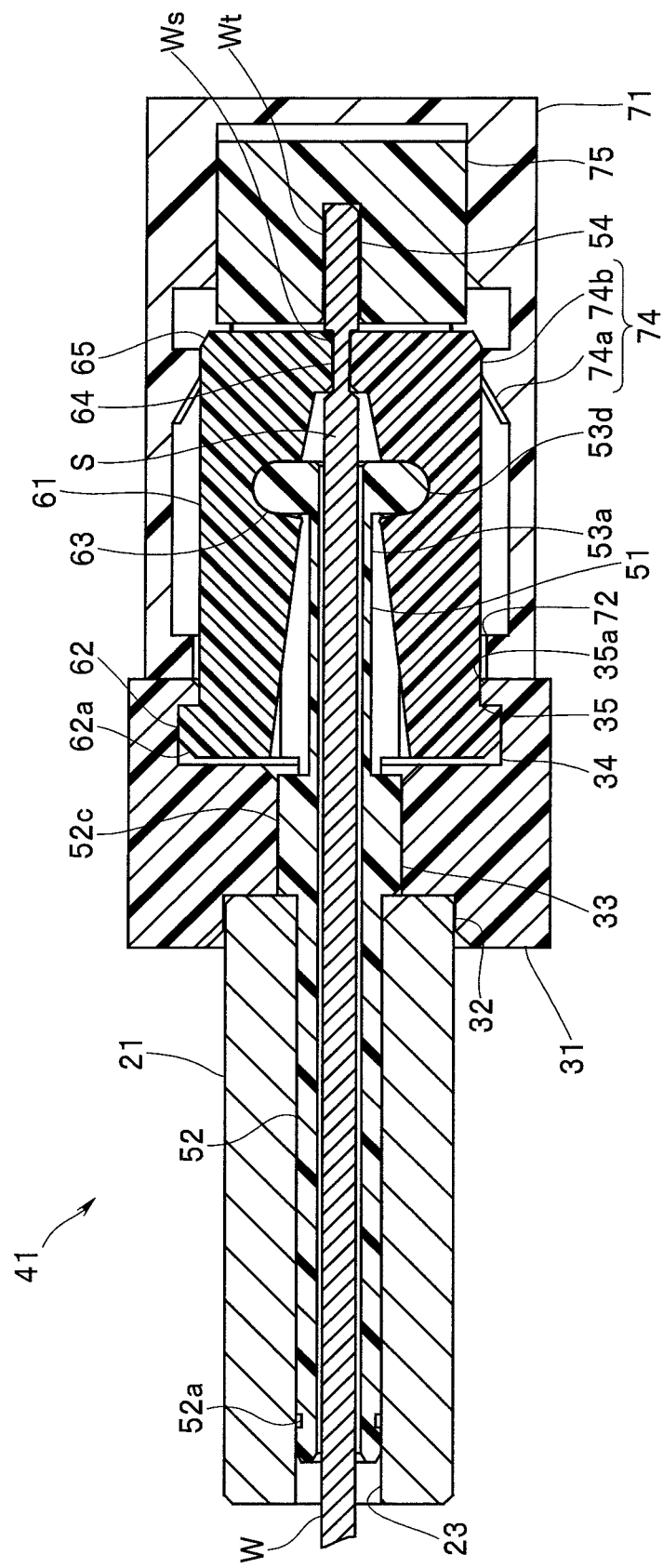
FIG. 8 is a cross-sectional view taken along a line VIII-VIII in FIG. 5 according to the embodiment of the present invention.

FIG. 5 is a view showing a proximal end surface of the connector 41 of the endoscope 1 according to the embodiment of the present invention. FIG. 6 is an exploded perspective view showing one example of the wire W, the cylinder 21, the ring 31 and the connector 41 of the endoscope 1. FIG. 7 is a cross-sectional view taken along a line VII-VII in FIG. 5 according to the embodiment of the present invention. FIG. 8 is a cross-sectional view taken along a line VIII-VIII in FIG. 5 according to the embodiment of the present invention.

The connector 41 is mounted on the operation section 4, and connects the wire W and the operation knob 11 to each other. FIG. 5 is a view of the connector 41 having a circular cylindrical shape which is mounted on the operation section 4 as viewed in a proximal end direction. In an example shown in FIG. 5, an outer periphery of the connector 41 has a circular shape. However, the shape of the outer periphery of the connector 41 is not limited to a circular shape and may be other shapes. As shown in FIG. 6, the connector 41 has the support member 51, the open-close members 61, and a fixing sleeve 71 which constitutes a locking member.

Although the support member 51 is not particularly limited, the support member 51 is made of a resin, for example. The support member 51 has a piston 52, an open-close member support portion 53, and a terminal accommodating portion 54.

The piston 52 is formed in an elongated sleeve shape, and is configured to be inserted into the cylinder 21. A circumferential groove 52a in which an O-shaped ring is mounted is formed on an outer peripheral surface of a distal end portion of the piston 52. The O-shaped ring slidably moves on an inner peripheral surface of the cylinder 21 along with the advancing or retracting movement of the piston 52.

A rotation stopping projection 52b is formed on the outer peripheral surface of a center portion of the piston 52 in a longitudinal direction (see FIG. 7). The rotation stopping projection 52b engages with the rotation stopper groove 22 and stops the rotation of the support member 51 in the circumferential direction. A projecting height of the rotation stopping projection 52b in a radial direction is set such that the rotation stopping projection 52b passes through the inside of the support member mounting portion 33 in a radial direction. A large-diameter portion 52c which has a diameter larger than a diameter of a center portion of the piston 52 in a longitudinal direction and is fitted in the support member mounting portion 33 is formed on the piston 52 on a proximal end side.

The open-close member support portion 53 is connected to a proximal end side of the piston 52. The open-close member support portion 53 includes a shaft sleeve 53a, support columns 53b, extending portions 53c, and support ribs 53d.

The shaft sleeve 53a is connected to the piston 52, and extends from the large-diameter portion 52c of the piston 52 in a longitudinal direction.

The support columns 53b are disposed to face each other with the shaft sleeve 53a sandwiched between the support columns 53b. Each of the support columns 53b has an approximately sector columnar shape where a sector shape continues in a longitudinal direction. Each of the support columns 53b is continuously formed with an outer peripheral surface of the shaft sleeve 53a such that a portion of the support column 53b which is positioned at the center of the sector shape faces the shaft sleeve 53a. Respective distal end surfaces of the support columns 53b butt against a deep portion of the hook accommodating portion 34.

Each of the support columns 53b has: two tapered surfaces 53e which are inclined to be gradually away from each other as the tapered surfaces 53e extend outwardly in a radial direction from the outer peripheral surface of the shaft sleeve 53a; and a circular arcuate surface 53f which is formed so as to connect outer edges of the two tapered surfaces 53e in a circumferential direction. The circular arcuate surface 53f is disposed inwardly in a radial direction with respect to a position along an inner peripheral surface of the inwardly directed flange and outwardly in the radial direction with respect to a position along an inner peripheral surface of the support member mounting portion 33.

Two protruding portions 53g are formed on the circular arcuate surface 53f in a spaced apart manner from each other in a circumferential direction, and a guide groove 53h is formed between the protruding portions 53g. The respective guide grooves 53h formed on the support columns 53b are arranged at positions where the guide grooves 53h face each other with the shaft sleeve 53a sandwiched between the guide grooves 53h.

The extending portions 53c extend from the respective proximal end portions of the support columns 53b in a proximal end direction. An arrangement space S for the wire W protruding from a proximal end opening of the shaft sleeve 53a is disposed between the respective extending portions 53c.

The support ribs 53d are disposed in a protruding manner from a proximal end portion of the shaft sleeve 53a such that the support ribs 53d face each other with the shaft sleeve 53a sandwiched between the support ribs 53d between the respective support columns 53b. The support ribs 53d support predetermined fulcrums of the open-close members 61.

The terminal accommodating portion 54 is connected to proximal end sides of the extending portions 53c. The terminal accommodating portion 54 has a cylindrical shape, and accommodates the terminal portion Wt of the wire W inserted from an opening on a distal end side. A long member positioning portion against which a proximal end of the wire W butts may be disposed on a deep portion of the terminal accommodating portion 54. By making a proximal end of the wire W butt against a long member positioning portion, the stepped portion Ws and the holding portion 64 are positioned. In the embodiment, the terminal accommodating portion 54 has a headed cylindrical shape. However, the terminal accommodating portion 54 may not have a head portion.

The open-close members 61 are mounted such that the open-close members 61 face each other so as to sandwich the shaft sleeve 53a between the open-close members 61 Each of the open-close members 61 is disposed between each of the support columns 53b in a longitudinal direction such that the open-close member 61 swings in a see-saw manner about a predetermined fulcrum which is supported by the support rib 53d. When the distal end portions of the open-close members 61 approach each other by a swing, the distal end portions are brought into a closed state and the proximal end portions are brought into an open state. On the other hand, when the proximal end portions of the open-close members 61 approach each other by a swing, the distal end portions are brought into an open state and the proximal end portions are brought into a closed state. Each of the open-close members 61 has a hook 62 which forms an engaging portion, a rib receiving portion 63, a holding portion 64, and a contact portion 65.

A hook 62 is formed on a distal end side of the open-close member 61 in an outwardly protruding manner in a radial direction such that the book 62 is inserted into the hook accommodating portion 34, and can be latched to the inwardly directed flange 35. A tapered guide 62a for entering the hook accommodating portion 34 is formed on a distal end surface of the hook 62 on an outer side in a radial direction.

The rib receiving portion 63 is formed on a portion of the open-close member 61 on a shaft sleeve side. The rib receiving portion 63 is formed in a U-shape groove shape which penetrates in a width direction such that the support ribs 53d can be inserted.

The holding portion 64 is formed on the open-close member 61 in a protruding manner from a proximal end side of the open-close member 61 in a direction toward the arrangement space S for the wire W such that the holding portion 64 can hold the stepped portion Ws of the wire W protruding from a proximal end opening of the shaft sleeve 53a.

The contact portion 65 is formed on a proximal end surface of the open-close member 61 on an outside in a radial direction. The contact portion 65 is formed on a portion of the fixing sleeve 71 with which a slider 74 is brought into contact. The contact portion 65 has a tapered shape.

Figure 9:
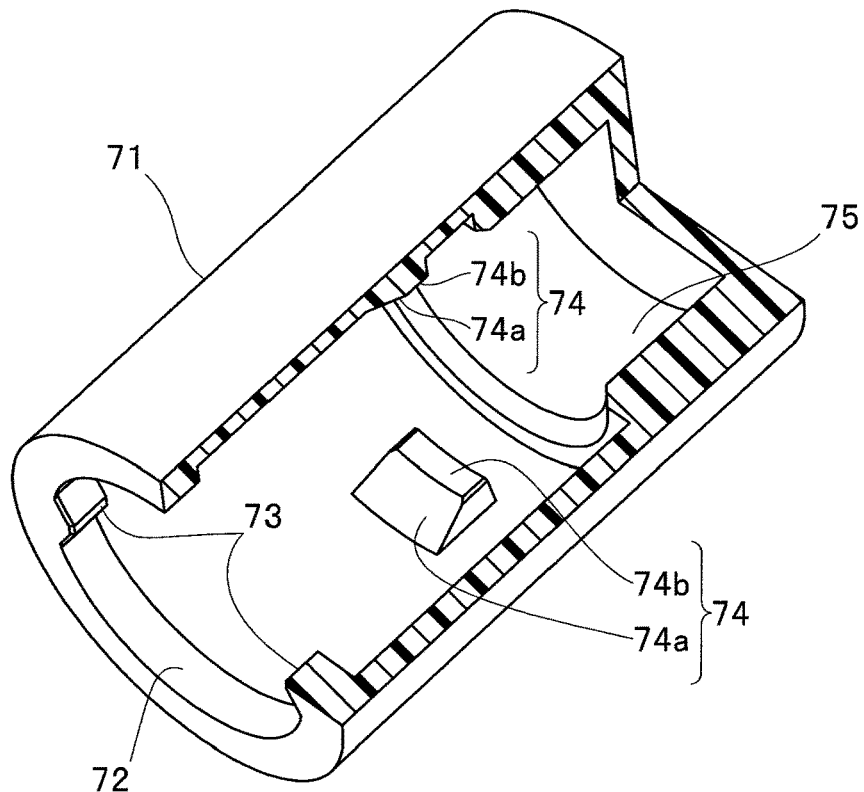
FIG. 9 is a perspective view of a cross section of a fixing sleeve in the connector of the endoscope according to the embodiment of the present invention.
Figure 10:
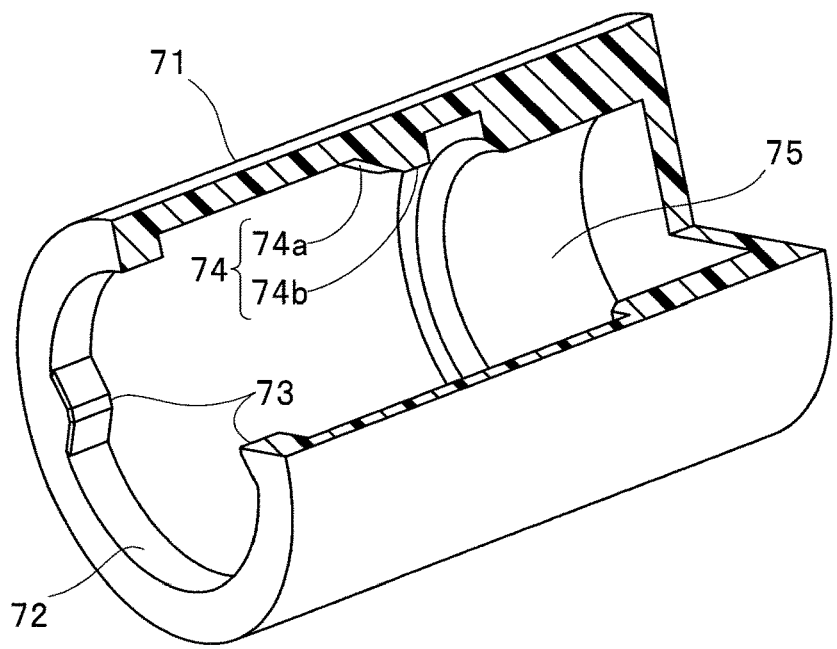
FIG. 10 is a perspective view of a cross section of the fixing sleeve in the connector of the endoscope according to the embodiment of the present invention.

FIG. 9 and FIG. 10 are perspective views of a cross section of the fixing sleeve 71 in the connector 41 of the endoscope 1 according to the embodiment of the present invention.

Although not particularly limited, the fixing sleeve 71 is made of a resin, for example. The fixing sleeve 71 has a headed sleeve shape. The fixing sleeve 71 is fitted on the support member 51 on which the open-close member 61 is mounted, to fix the wire W to the connector 41. The fixing sleeve 71 includes an opening portion 72, inwardly directed projecting portions 73, sliders 74 each of which is a restricting portion, and a support member accommodating portion 75.

The opening portion 72 is formed on a distal end side of the fixing sleeve 71. An inner peripheral surface f the opening portion 72 is disposed outside in a radial direction with respect to a position along an outer peripheral surface of the protruding portion 53g formed on the circular arcuate surface 53f.

The inwardly directed projecting portions 73 are formed on the inner peripheral surface of the opening portion 72 such that the inwardly directed projecting portions 73 face each other. The respective inwardly directed projecting portions 73 are disposed at positions corresponding to the guide grooves 53h such that the respective inwardly directed projecting portions 73 are fitted on the support member 51 depending on preset rotary positions. The respective inwardly directed projecting portions 73 are disposed outside in a radial direction with respect to the position along the circular arcuate surface 53f and inside in a radial direction with respect to the position along the outer peripheral surface of the protruding portions 53g. The respective inwardly directed projecting portions 73 have a predetermined inner width therebetween. The predetermined inner width is set to an inner width smaller than an inner diameter of the inwardly directed flange 35 such that the respective inwardly directed projecting portions 73 can press a portion of the open-close member 61 on a distal end portion side along with the rotation in a circumferential direction.

The sliders 74 are formed on an inner peripheral surface of the fixing sleeve 71 in a protruding manner such that the sliders 74 face each other in the vicinity of a center portion of the inner peripheral surface of the fixing sleeve 71 in a longitudinal direction. The rotational position of the sliders 74 is set such that the rotational position of the sliders 74 is aligned with the rotational position of the open-close members 61 when the rotational positions of the inwardly directed projecting portions 73 and the guide grooves 53h are aligned with each other. For example, when the pair of open-close members 61 is arranged at the positions rotated by 90 degrees from the pair of guide grooves 53h, the pair of sliders 74 is also arranged at the position rotated by 90 degrees from the pair of inwardly directed projecting portions 73.

Each of the sliders 74 has a slide tapered portion 74a and a pressing portion 74b.

The slide tapered portion 74a is disposed at the position where the slide tapered portion 74a is brought into contact with the contact portion 65 when a proximal end portion of the open-close member 61 is brought into an open state on a distal end side of the slider 74. The slide tapered portion 74a is inclined so as to approach inwardly in a radial direction as the slide tapered portion 74a extends toward a proximal end direction. When the slide tapered portion 74a is brought into contact with the contact portion 65, the contact portion 65 is moved inwardly in the radial direction thus bringing the proximal end portion of the open-close member 61 into a closed state and the distal end portion of the open-close member 61 into an open state.

The pressing portion 74b is continuously formed on the proximal end side of the slide tapered portion 74a. The pressing portion 74b protrudes inwardly in the radial direction from an inner peripheral surface of the fixing sleeve 71, and presses the proximal end portion of the open-close member 61 such that the holding portion 64 is not opened.

The support member accommodating portion 75 has an inner peripheral surface along an outer peripheral surface of the support member 51, and accommodates the proximal end portion of the support member 51.

In other words, the connector 41 connects the ring 31 and the wire W to each other. The connector 41 includes the open-close members 61 and the fixing sleeve 71. The open-close member 61 has the distal end portion and the proximal end portion which are opened or closed along with swing of the open-close member 61 about the predetermined fulcrum. The holding portion 64 which holds the wire W when the proximal end portion is closed is formed on the proximal end portion, and the hook 62 which projects outwardly in the radial direction of the distal end portion and is engageable with the inside of the ring 31 is formed on the distal end portion. The fixing sleeve 71 moves in a longitudinal direction outside the open-close member 61 in the radial direction, and locks the proximal end portion of the open-close member 61 and the ring 31 in a state where the wire W is held.

The fixing sleeve 71 includes the slider 74 which is brought into contact with the open-close member 61 such that the slider 74 restricts the operation of the opened or closed open-close member 61 by the fixing sleeve 71 moving in a longitudinal direction. More specifically, the fixing sleeve 71 is formed in a shape so as to cover a periphery of the open-close member 61.

The inwardly directed flanges 35 which protrude inwardly in a radial direction are disposed in the ring 31. When the fixing sleeve 71 moves in a distal end direction in a state where the open-close member 61 holds the wire W, the hook 62 engages with the inwardly directed flanges 35.

The open-close member 61 swings in a see-saw manner about the predetermined fulcrum, and the open-close member 61 is switched between a holding state and a holding release state of the stepped portion Wx by the proximal end portion in response to opening or closing of the proximal end portion. The open-close member 61 swings in a see-saw manner about the predetermined fulcrum, and is switched between an engagement state and an engagement release state of the hook 62 and the ring 31 in response to opening or closing of the proximal end portion.

The connector 41 has the shaft sleeve 53a having a passage through which the wire W is guided into the open-close member 61, and a support rib 53d which supports the predetermined fulcrum of the open-close member 61 is formed on an outer peripheral surface of the shaft sleeve 53a.

(Operation)

Next, one example of a method of mounting the wire W is described.

Figure 16:
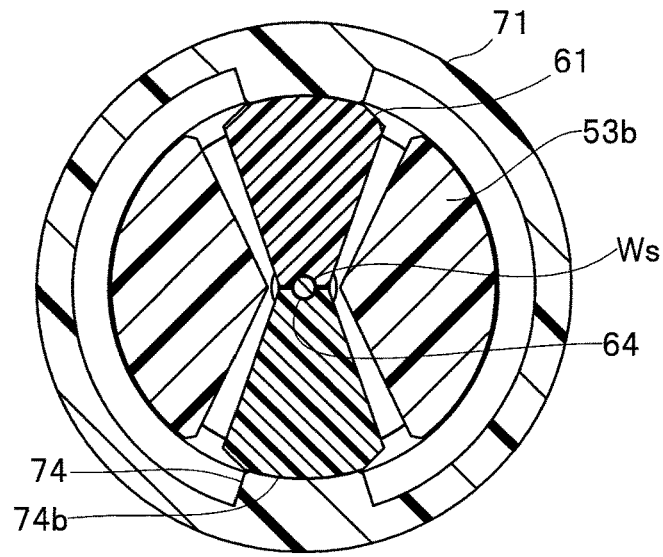
FIG. 16 is a cross-sectional view taken along a line XVI-XVI in FIG. 15 according to the embodiment of the present invention.
Figure 17:
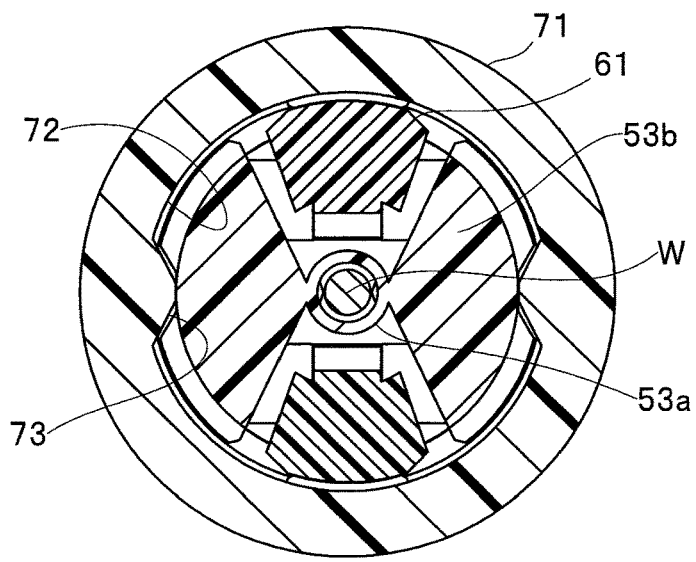
FIG. 17 is a cross-sectional view taken along a line XVII-XVII in FIG. 15 according to the embodiment of the present invention.

FIG. 11 to FIG. 15 are explanatory diagrams describing one example of a method of mounting the wire W using the connector 41 of the endoscope 1 according to the embodiment of the present invention. FIG. 16 is a cross-sectional view taken along a line XVI-XVI in FIG. 15 according to the embodiment of the present invention. FIG. 17 is a cross-sectional view taken along a line XVII-XVII in FIG. 15 according to the embodiment of the present invention.

A user rotatably operates the operation knob 11 so as to move the ring 31 in a direction toward the operation section 4 thus bringing about a state where the ring 31 is mounted on an outer side of the proximal end portion of the cylinder 21. The user inserts the wire W into the guide conduit 5c and makes the wire W protrude from the cylinder 21 and the ring 31.

Figure 11:
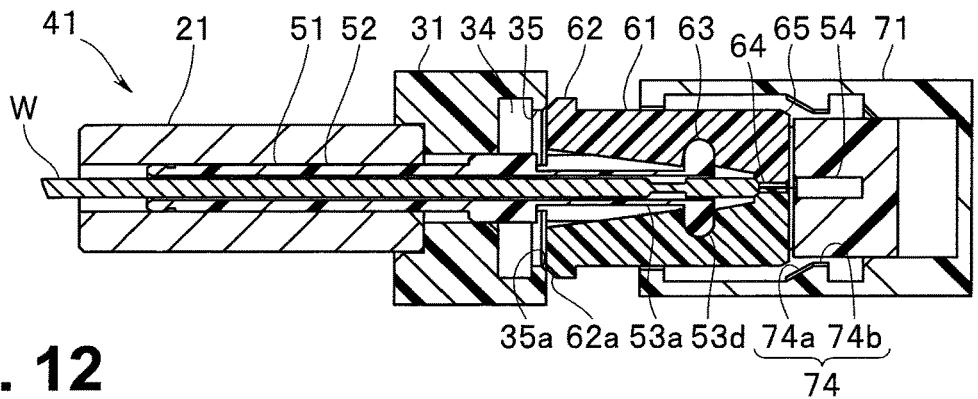
FIG. 11 is an explanatory diagram describing one example of a method of attaching a wire using the connector of the endoscope according to the embodiment of the present invention.
Figure 12:
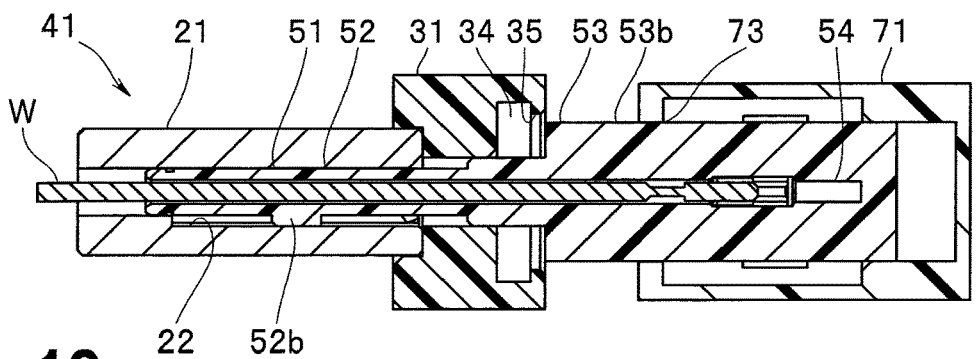
FIG. 12 is an explanatory diagram describing one example of the method of attaching the wire using the connector of the endoscope according to the embodiment of the present invention.

As shown in FIG. 11 and FIG. 12, the user grasps the connector 41, inserts the wire W into the piston 52, makes the rotation stopping projection 52b aligned with the rotation stopper groove 22, and inserts the piston 52 into the cylinder 21.

Figure 13:
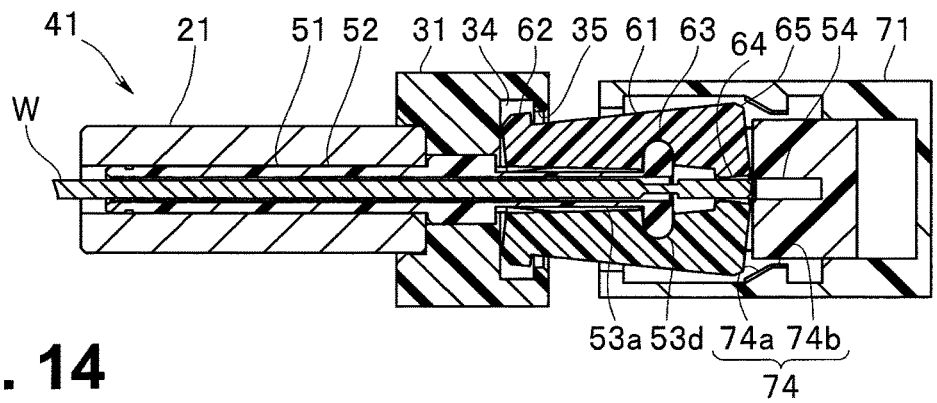
FIG. 13 is an explanatory diagram describing one example of the method of attaching the wire using the connector of the endoscope according to the embodiment of the present invention.

As shown in FIG. 13, when the user pushes the fixing sleeve 71 in a distal end direction, the support member 51 and the open-close members 61 are pressed by the fixing sleeve 71 and are also moved in the distal end direction. The tapered guides 62a of the open-close members 61 are brought into contact with the tapered guide 35a of the ring 31, the respective distal end portions of the open-close members 61 are moved inwardly in the radial direction, the hooks 62 pass inside the inwardly directed flange 35 in the radial direction, and are accommodated in the hook accommodating portion 34.

Figure 14:
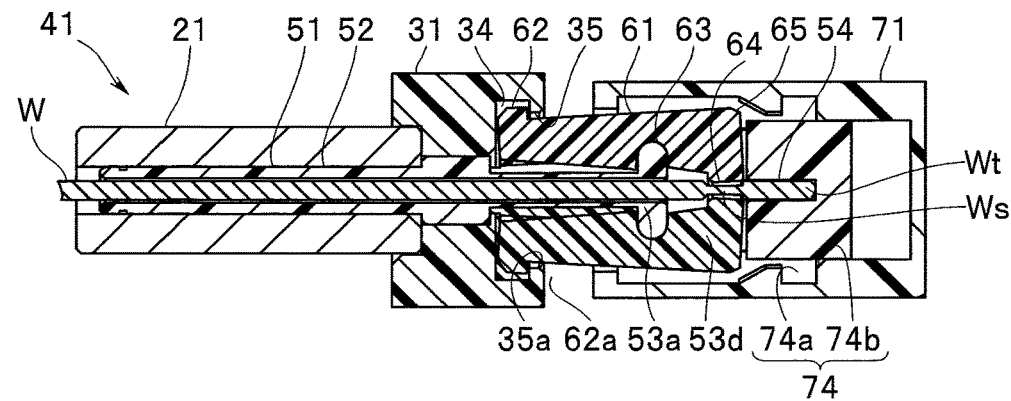
FIG. 14 is an explanatory diagram describing one example of the method of attaching the wire using the connector of the endoscope according to the embodiment of the present invention.

When the distal end portion of the open-close member 61 is brought into a closed state, the proximal end portions of the open-close members 61 are brought into an open state because of swinging of the open-close members 61 about the predetermined fulcrums supported by the support ribs 53d. As shown in FIG. 14, when the user pushes the fixing sleeve 71, the terminal portion Wt is accommodated in the terminal accommodating portion 54.

Figure 15:
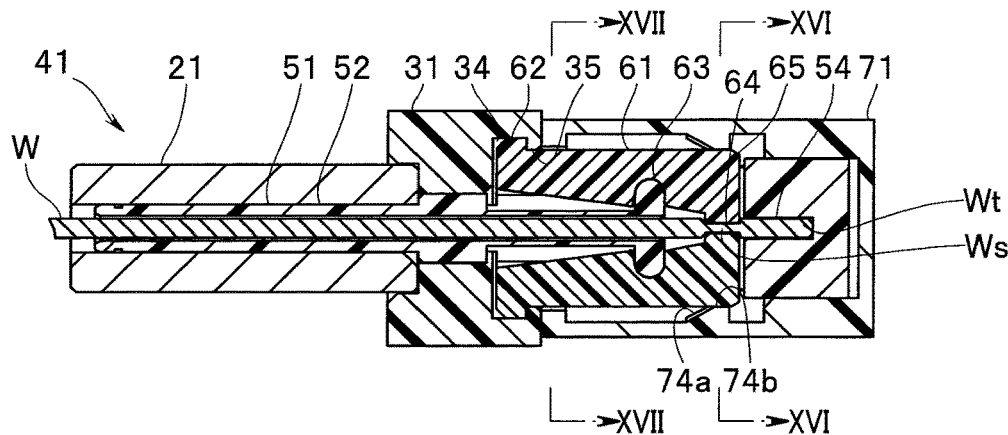
FIG. 15 is an explanatory diagram describing one example of the method of attaching the wire using the connector of the endoscope according to the embodiment of the present invention.

As shown in FIG. 15, when the user pushes the fixing sleeve 71 in a distal end direction, the slide tapered portions 74a are brought into contact with the contact portions 65, and the respective proximal end portions of the open-close members 61 are moved inwardly in the radial direction. When the user further pushes the fixing sleeve 71 in the distal end direction, as shown in FIG. 16, the pressing portions 74b press the proximal end portions of the open-close members 61, and the holding portions 64 hold the stepped portion Ws. As shown in FIG. 17, the respective inwardly directed projecting portions 73 are arranged at the rotary positions displaced by 90 degrees from the open-close member 61.

When the proximal end portions of the open-close members 61 are brought into a closed state, the distal end portions of the open-close members 61 are brought into an open state. The hooks 62 move outwardly in the radial direction, and are latched to the inwardly directed flange 35.

A relationship of F1<F2 is established, where F1 indicates a force necessary for pushing the wire W by the connector 41 and F2 indicates a force necessary for the fixing sleeve 71 to move the proximal end portions of the open-close members 61 inwardly in the radial direction.

When the support member 51, the open-close members 61 and the fixing sleeve 71 are mounted on the ring 31, the operation section 4 and the wire W are connected to each other.

In other words, in the method of mounting the wire W, the proximal end portions of the open-close members 61 are opened and the distal end portions of the open-close members 61 are closed by swinging the open-close members 61 about the predetermined fulcrums, the wire W is inserted into the open-close members 61 where the proximal end portions are opened, the closed distal end portions are inserted into the ring 31 connected to the operation section 4, the fixing sleeve 71 is moved in a longitudinal direction radially outside with respect to the open-close members 61, the proximal end portions of the open-close members 61 which are opened because of the engagement of the open-close members 61 with the fixing sleeve 71 are closed, and the closed distal end portions of the open-close member 61 are opened, the opened distal end portions engage with the ring 31, and the wire W is held by the closed proximal end portions.

Next, one example of a method of detaching the wire W is described.

Figure 18:
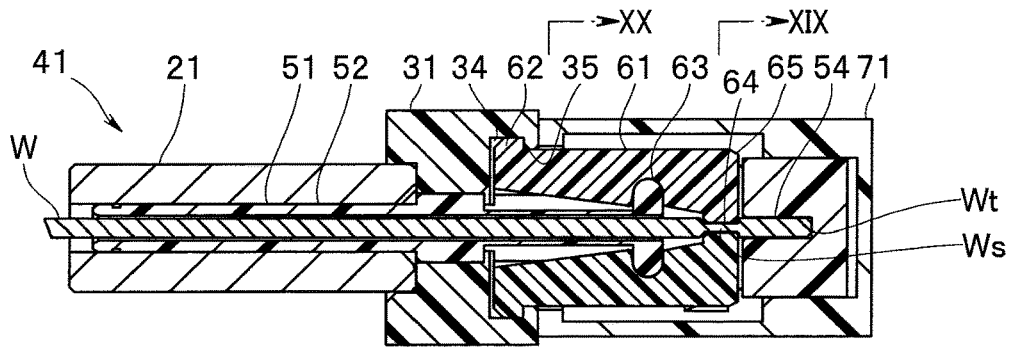
FIG. 18 is an explanatory diagram describing one example of a method of detaching the wire using the connector of the endoscope according to the embodiment of the present invention.
Figure 19:
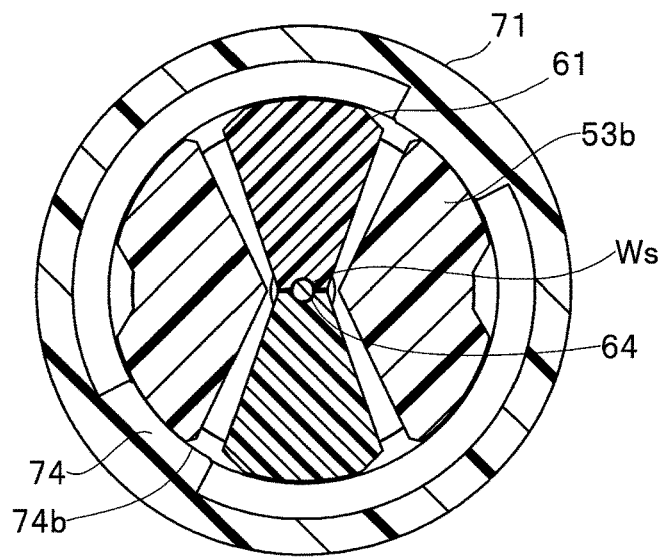
FIG. 19 is a cross-sectional view taken along a line XX-XIX in FIG. 18 according to the embodiment of the present invention.
Figure 20:
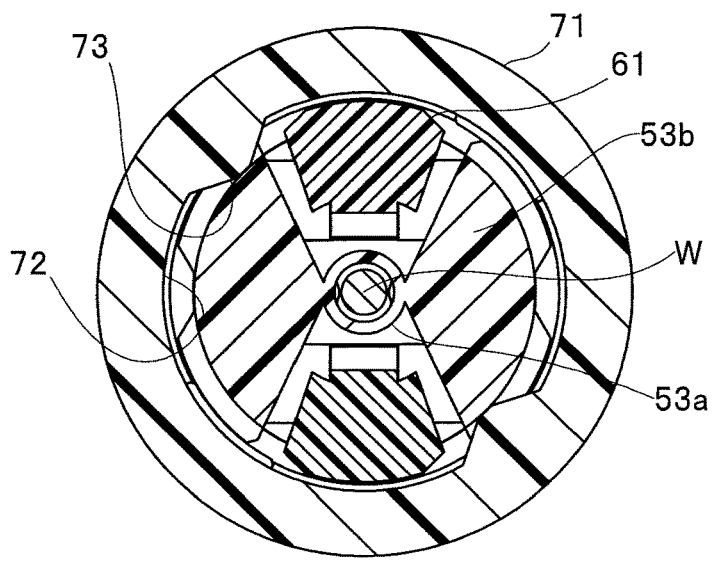
FIG. 20 is a cross-sectional view taken along a line XX-XX in FIG. 18 according to the embodiment of the present invention.
Figure 21:
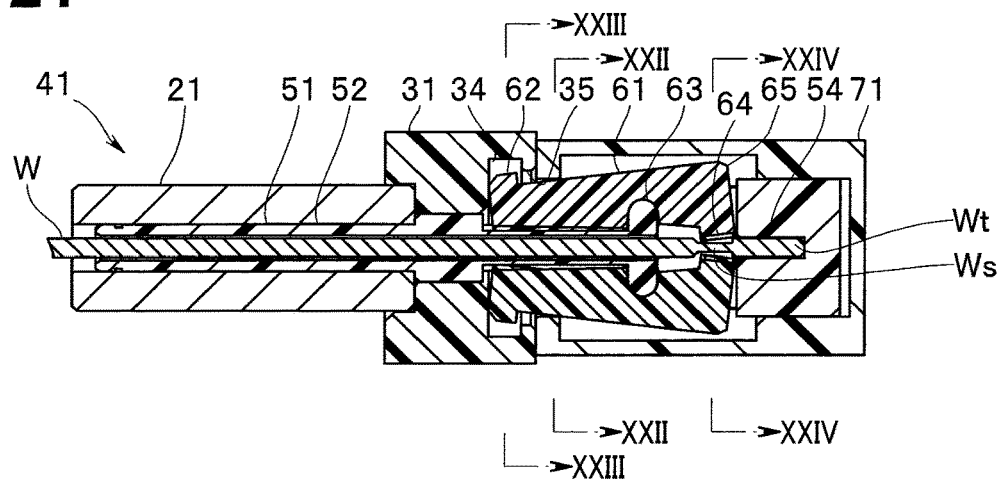
FIG. 21 is an explanatory diagram describing one example of the method of detaching the wire using the connector of the endoscope according to the embodiment of the present invention.
Figure 22:
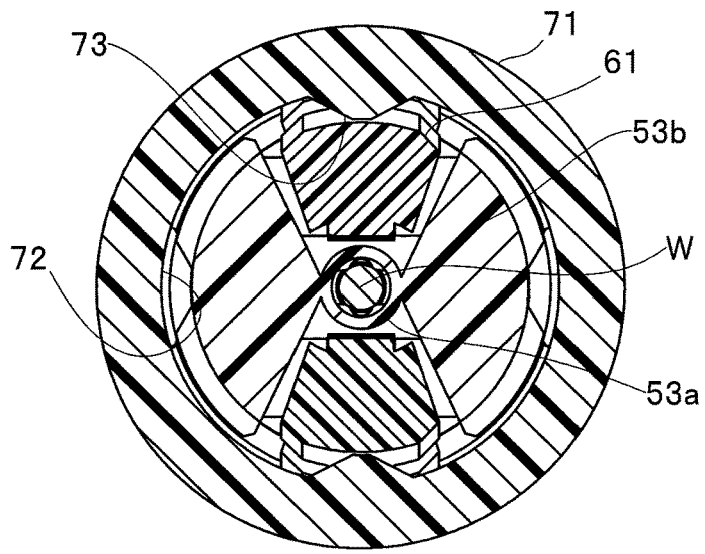
FIG. 22 is a cross-sectional view taken along a line XXII-XXII in FIG. 21 according to the embodiment of the present invention.
Figure 23:
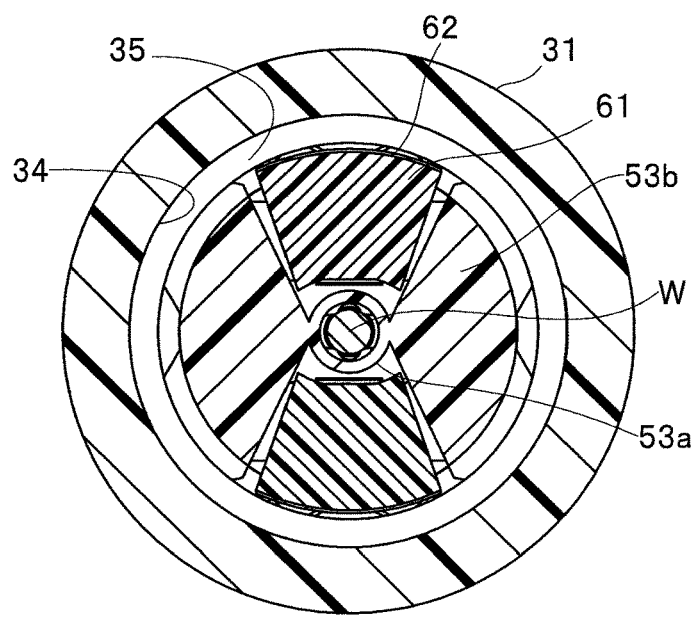
FIG. 23 is a cross-sectional view taken along a line XXII-XXIII in FIG. 21 according to the embodiment of the present invention.
Figure 24:
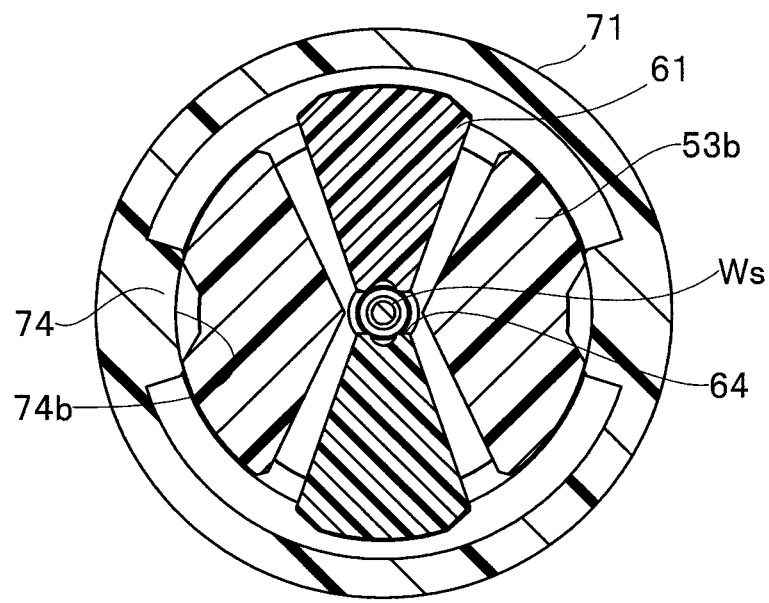
FIG. 24 is a cross-sectional view taken along a line XXIV-XXV in FIG. 21 according to the embodiment of the present invention.

FIG. 18 is an explanatory diagram describing one example of a method of detaching the wire W using the connector 41 of the endoscope 1 according to the embodiment of the present invention. FIG. 19 is a cross-sectional view taken along a line XIX-XIX in FIG. 18 according to the embodiment of the present invention. FIG. 20 is a cross-sectional view taken along a line XX-XX in FIG. 18 according to the embodiment of the present invention. FIG. 21 is an explanatory diagram describing one example of the method of detaching the wire W using the connector 41 of the endoscope 1 according to the embodiment of the present invention. FIG. 22 is a cross-sectional view taken along a line XXII-XXII in FIG. 21 according to the embodiment of the present invention. FIG. 23 is a cross-sectional view taken along a line XXII-XXIII in FIG. 21 according to the embodiment of the present invention. FIG. 24 is a cross-sectional view taken along a line XXIV-XXIV in FIG. 21 according to the embodiment of the present invention.

The user grasps the fixing sleeve 71, and rotates the fixing sleeve 71 in a circumferential direction. When the fixing sleeve 71 is rotated, the pressing portions 74b are removed from the proximal end portions of the open-close members 61 (FIG. 18, FIG. 19), and the inwardly directed projecting portions 73 are moved to approach the open-close members 61.

As shown in FIG. 21 and FIG. 22, when the user further rotates the fixing sleeve 71 in a circumferential direction, the inwardly directed projecting portions 73 push the open-close members 61 so as to move the open-close members 61 inwardly in a radial direction. As shown in FIG. 23, the hooks 62 are moved inwardly in a radial direction with respect to the position along the inner peripheral surface of the inwardly directed flange 35.

As shown in FIG. 24, when the distal end portions of the open-close members 61 are brought into a closed state by the rotation of the fixing sleeve 71, the proximal end portions of the open-close members 61 are brought into an open state. The respective holding portions 64 are moved outwardly in the radial direction, and are separated from the stepped portion Ws. When the user grasps the fixing sleeve 71 and moves the fixing sleeve 71 in a proximal end direction, the connector 41 is detached from the operation section 4 and hence, the connection between the wire W and the operation section 4 is released. Accordingly, the user can detach the treatment instrument raising base 8 and the wire W from the endoscope 1.

In other words, the holding portions 64 hold a portion of the periphery of the wire W, the fixing sleeve 71 is configured to be rotatable around the wire W. and by releasing the contact between the sliders 74 and the open-close members 61 by rotating the fixing sleeve 71, the fixing sleeve 71 is brought into a state where the fixing sleeve 71 is movable in a proximal end direction.

The connector 41 is configured to be detachable by a rotation operation of the fixing sleeve 71, and prevents the wire W from dropping off during insertion of the endoscope 1 into a subject.

According to the embodiment, in the endoscope 1, the wire W which is connected to the operation member mounted on the insertion section distal end portion D can be more easily and properly attached to the operation section 4.

In the embodiment, a locking portion is not formed on an inner peripheral surface of the support member accommodating portion 75 and an outer peripheral surface of the terminal accommodating portion 54. However, for example, a locking portion such as a small circumferential groove or a small circumferential projection may be formed, and when inserting the terminal accommodating portion 54 into the support member accommodating portion 75, a click feeling may be given to a user. Further, a locking portion such as a locking pawl or the like may be formed so that dropping-off may be prevented after the terminal accommodating portion 54 is inserted into the support member accommodating portion 75.

In the embodiment, a seal member is not disposed on the inner peripheral surface of the fixing sleeve 71. However, a seal member may be disposed so as to prevent leaking of a fluid which flows reversely in the guide conduit 5c and the support member 51.

In the embodiment, the connector 41 and the wire W of the embodiment may be disposable.

The present invention is not limited to the above-mentioned embodiment, and various modifications and alterations can be made without departing from the gist of the present invention.

According to the present invention, it is possible to provide an endoscope and a method of attaching a long member where the long member which is connected to an operation member mounted on an insertion section distal end portion can be more easily and properly attached on an operation section.

What is claimed is:

1. An endoscope comprising:
    an operation body disposed on an insertion section,
    a wire connected to the operation body, the wire being configured to move in a longitudinal direction of the insertion section so as to operate the operation body,
    a movable body disposed on an operation section, the movable body being disposed proximally relative to the insertion section,
    an operation knob disposed on the operation section, the operation knob being configured to move the movable body, and
    a connector disposed on the operation section, the connector connecting the movable body and the wire to each other, wherein the connector includes:
        an open-close body having a first end portion and a second end portion which are opened and closed by swinging about a predetermined fulcrum, the second end portion having a holding portion which holds the wire when the second end portion is closed, the first end portion having an outer surface and a projection projecting outward from the outer surface in a radial direction of the first end portion and the projection is engageable with an inner side of the movable body; and
        a locking body configured to move outwardly in a longitudinal direction of a proximal end portion of the wire, and to lock the open-close body and the movable body with each other in a state where the wire is held by the second end portion of the open-close body.

2. The endoscope according to claim 1, wherein the locking body includes a restricting portion configured to contact with the open-close body so as to restrict an operation of the open-close body which is opened or closed, by the locking body moving in the longitudinal direction of the proximal end portion of the wire.

3. The endoscope according to claim 2, wherein the holding portion is configured to hold a portion of a periphery of the wire, the locking body is rotatably disposed around the wire, and the wire is brought into a released state where the locking body is moved in a proximal end direction to release contact between the restricting portion and the open-close body by rotating the locking body.

4. The endoscope according to claim 1, wherein the locking body having a shape to cover a periphery of the open-close body.

5. The endoscope according to claim 1, wherein an inner side of the movable body includes an inwardly directed flange projecting radially inward, and
    the projection is configured to engage with the inwardly directed flange when the locking body moves in a distal end direction in a state where the open-close body holds the wire.

6. The endoscope according to claim 1, wherein the proximal end portion of the wire includes an open-close body engaging portion which engages with the holding portion.

7. The endoscope according to claim 6, wherein each of the first end portion and the second end portion of the open-close body is configured to rotate about the predetermined fulcrum, and switches to either a holding state or a holding release state of the open-close body engaging portion by the second end portion according to opening or closing of the second end portion.

8. The endoscope according to claim 6, wherein each of the first end portion and the second end portion of the open-close body is configured to rotate in a see-saw manner about the predetermined fulcrum, and switches to either an engaging state or an engaging release state with the movable body by the projection according to opening or closing of the second end portion.

9. The endoscope according to claim 6, wherein the open-close body engaging portion of the wire has a smaller diameter than other portions of the wire.

10. The endoscope according to claim 1, wherein the connector includes a wire positioning portion which butts against an end portion of the wire.

11. The endoscope according to claim 1, wherein a relationship of F1<F2 is established, where F1 indicates a force necessary for pushing the wire by the connector and F2 indicates a force necessary for the locking body to move the second end portion of the open-close body inwardly in a radial direction.

12. The endoscope according to claim 1, wherein the connector includes a shaft sleeve having a passage through which the wire is guided into the open-close body, and a support rib, which supports the predetermined fulcrum of the open-close body, is formed on an outer peripheral surface of the shaft sleeve.

13. The endoscope according to claim 1, wherein the operation body is a treatment instrument raising base which changes a direction of a treatment instrument which passes through the insertion section.

14. The endoscope according to claim 1, wherein the operation knob comprising:
   a knob body being rotatable about a rotary shaft;
   a rotary body rotatable with the rotary shaft about a center position of the rotary body, the rotary body configured to transmit a rotational force from the rotary shaft; and
   a rod including a first end and a second end, the first end being rotatably connected to a periphery portion of the rotary body, the second end being rotatably connected to the movable body, the rod converting a rotary movement of the rotary body into a linear movement and transmitting the linear movement to the movable body.

15. The endoscope according to claim 1, wherein the locking body comprising:
   an opening portion formed on a distal end side of the locking body;
   a plurality of inwardly directed projecting portions formed on an inner peripheral surface of the opening portion; and
   a restricting portion formed on an inner peripheral surface of the locking body, the restricting portion protruding inwardly.

16. The endoscope according to claim 15, wherein the projecting portions and the restricting portions are offset circumferentially relative to each other.

17. The endoscope according to claim 1, wherein the movable body being configured to move in the longitudinal direction of the insertion section.

18. The endoscope according to claim 1, wherein the first end portion is a distal end portion of the open-close body and the second end portion is a proximal end portion of the open-close body.

19. An endoscope comprising:
   an operation body disposed on an insertion section,
   a wire connected to the operation body, the wire being configured to move in a longitudinal direction of the insertion section so as to operate the operation body,
   a movable body disposed on an operation section, the movable body being disposed proximally relative to the insertion section,
   an operation knob disposed on the operation section, the operation knob being configured to move the movable body, and
   a connector disposed on the operation section, the connector connecting the movable body and the wire to each other, wherein the connector includes:
      an open-close body having a first end portion and a second end portion which are opened and closed by swinging about a predetermined fulcrum, the second end portion having a holding portion which holds the wire when the second end portion is closed, the first end portion having an engaging portion which projects outwardly in a radial direction of the first end portion and is engageable with an inner side of the movable body; and
      a locking body configured to move outwardly in a longitudinal direction of a proximal end portion of the wire, and to lock the open-close body and the movable body with each other in a state where the wire is held by the second end portion of the open-close body;
   wherein the open-close body is configured to swing in a see-saw manner about the predetermined fulcrum, and switches to either an engaging state or an engaging release state with the movable body by the engaging portion according to opening or closing of the second end portion.

20. An endoscope comprising:
   an operation body disposed on an insertion section,
   a wire connected to the operation body, the wire being configured to move in a longitudinal direction of the insertion section so as to operate the operation body,
   a movable body disposed on an operation section, the movable body being disposed proximally relative to the insertion section,
   an operation knob disposed on the operation section, the operation knob being configured to move the movable body, and
   a connector disposed on the operation section, the connector connecting the movable body and the wire to each other, wherein the connector includes:
      an open-close body having a first end portion and a second end portion which are opened and closed by swinging about a predetermined fulcrum, the second end portion having a holding portion which holds the wire when the second end portion is closed, the first end portion having an outer surface and a projection projecting outward from the outer surface in a radial direction of the first end portion and is engageable with an inner side of the movable body; and
      a locking body configured to move outwardly in a longitudinal direction of a proximal end portion of the wire, and to lock the open-close body and the movable body with each other in a state where the wire is held by the second end portion of the open-close body;
   wherein each of the first end portion and the second end portion of the open-close body is configured to rotate about the predetermined fulcrum, and switches to either a holding state or a holding release state of the open-close body engaging portion by the second end portion according to opening or closing of the second end portion.

* * * * *